US008328776B2

(12) United States Patent
Kelch et al.

(10) Patent No.: US 8,328,776 B2
(45) Date of Patent: Dec. 11, 2012

(54) REDUCED PRESSURE TREATMENT SYSTEM HAVING BLOCKAGE CLEARING AND DUAL-ZONE PRESSURE PROTECTION CAPABILITIES

(75) Inventors: Randall P. Kelch, San Antonio, TX (US); Xiaolu Zheng, San Antonio, TX (US); Reuben W. Edgar, Jr., San Antonio, TX (US); Jonathan Paul Jaeb, Boerne, TX (US); Thomas Paul Lawhorn, San Antonio, TX (US); Shannon C Ingram, Bulverde, TX (US)

(73) Assignee: KCI Licensing, Inc., San Antonio, TX (US)

( * ) Notice: Subject to any disclaimer, the term of this patent is extended or adjusted under 35 U.S.C. 154(b) by 243 days.

(21) Appl. No.: 12/824,582

(22) Filed: Jun. 28, 2010

(65) Prior Publication Data

US 2010/0268179 A1 Oct. 21, 2010

Related U.S. Application Data

(62) Division of application No. 11/903,165, filed on Sep. 19, 2007, now Pat. No. 7,758,555.

(60) Provisional application No. 60/849,138, filed on Oct. 2, 2006, provisional application No. 60/845,993, filed on Sep. 19, 2006.

(51) Int. Cl.
 *A61M 1/00* (2006.01)
(52) U.S. Cl. ........................ 604/313; 604/319
(58) Field of Classification Search .................. 604/313, 604/319, 543
See application file for complete search history.

(56) References Cited

U.S. PATENT DOCUMENTS

| | | | |
|---|---|---|---|
| 1,355,846 A | 10/1920 | Rannells |
| 1,885,926 A | 6/1931 | Lewis |
| 2,378,849 A | 6/1945 | Helleberg |
| 2,381,821 A | 8/1945 | Helleberg et al. |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,376,868 A | 4/1968 | Mondiadis |

(Continued)

FOREIGN PATENT DOCUMENTS

AU 550575 A1 8/1982

(Continued)

OTHER PUBLICATIONS

Final Office Action date mailed Oct. 29, 2010 for U.S. Appl. No. 12/069,364.

(Continued)

*Primary Examiner* — Susan Su

(57) ABSTRACT

A method of treating a tissue site is provided. The method includes applying a reduced pressure to a tissue site with a reduced pressure source. A source pressure is monitored at the reduced pressure source, and a differential pressure is determined between the source pressure and the desired tissue site pressure. If a blockage is present between the reduced pressure source and the tissue site, the differential pressure is limited to a first maximum differential pressure. If no blockage is present between the reduced pressure source and the tissue site, the differential pressure is limited to a second maximum differential pressure.

9 Claims, 2 Drawing Sheets

U.S. PATENT DOCUMENTS

| | | |
|---|---|---|
| 3,419,006 A | 12/1968 | King |
| 3,520,300 A | 7/1970 | Flower, Jr. |
| 3,568,675 A | 3/1971 | Harvey |
| 3,585,861 A | 6/1971 | Keng |
| 3,648,692 A | 3/1972 | Wheeler |
| 3,682,180 A | 8/1972 | McFarlane |
| 3,742,952 A | 7/1973 | Magers et al. |
| 3,744,306 A | 7/1973 | Krueger |
| 3,774,611 A | 11/1973 | Tussey et al. |
| 3,779,243 A | 12/1973 | Tussey et al. |
| 3,799,702 A | 3/1974 | Weishaar |
| 3,826,254 A | 7/1974 | Mellor |
| 3,892,229 A | 7/1975 | Taylor et al. |
| 4,080,970 A | 3/1978 | Miller |
| 4,091,804 A | 5/1978 | Hasty |
| 4,096,853 A | 6/1978 | Weigand |
| 4,139,004 A | 2/1979 | Gonzalez, Jr. |
| 4,141,361 A | 2/1979 | Snyder |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,375,217 A | 3/1983 | Arkans |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,901 A | 10/1984 | Kraegen et al. |
| 4,475,909 A | 10/1984 | Eisenberg |
| 4,480,638 A | 11/1984 | Schmid |
| 4,509,959 A | 4/1985 | McCombs |
| 4,525,166 A | 6/1985 | Leclerc |
| 4,525,374 A | 6/1985 | Vaillancourt |
| 4,529,402 A | 7/1985 | Weilbacher et al. |
| 4,534,756 A | 8/1985 | Nelson |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,553,431 A | 11/1985 | Nicolai |
| 4,569,348 A | 2/1986 | Hasslinger |
| 4,569,674 A | 2/1986 | Phillips et al. |
| 4,600,015 A | 7/1986 | Evans et al. |
| 4,605,399 A | 8/1986 | Weston et al. |
| 4,608,041 A | 8/1986 | Nielsen |
| 4,640,688 A | 2/1987 | Hauser |
| 4,650,462 A | 3/1987 | DeSatnick et al. |
| 4,655,754 A | 4/1987 | Richmond et al. |
| 4,664,652 A | 5/1987 | Weilbacher |
| 4,664,662 A | 5/1987 | Webster |
| 4,698,060 A | 10/1987 | D'Antonio et al. |
| 4,710,165 A | 12/1987 | McNeil et al. |
| 4,713,052 A | 12/1987 | Beck et al. |
| 4,722,332 A | 2/1988 | Saggers |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,798,583 A | 1/1989 | Beck et al. |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,917,112 A | 4/1990 | Kalt |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,981,474 A | 1/1991 | Bopp et al. |
| 4,985,019 A | 1/1991 | Michelson |
| 5,000,741 A | 3/1991 | Kalt |
| 5,001,924 A | 3/1991 | Walter et al. |
| 5,037,397 A | 8/1991 | Kalt et al. |
| 5,055,198 A | 10/1991 | Shettigar |
| 5,086,170 A | 2/1992 | Luheshi et al. |
| 5,092,858 A | 3/1992 | Benson et al. |
| 5,100,396 A | 3/1992 | Zamierowski |
| 5,106,629 A | 4/1992 | Cartmell et al. |
| 5,112,323 A | 5/1992 | Winkler et al. |
| 5,134,994 A | 8/1992 | Say |
| 5,149,331 A | 9/1992 | Ferdman et al. |
| 5,160,315 A | 11/1992 | Heinecke et al. |
| 5,167,613 A | 12/1992 | Karami et al. |
| 5,176,663 A | 1/1993 | Svedman et al. |
| 5,195,995 A | 3/1993 | Walker |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,358,494 A | 10/1994 | Svedman |
| 5,380,294 A | 1/1995 | Persson |
| 5,423,737 A | 6/1995 | Cartmell et al. |
| 5,429,593 A | 7/1995 | Matory |
| 5,435,009 A | 7/1995 | Schild et al. |
| 5,437,622 A | 8/1995 | Carion |
| 5,437,651 A | 8/1995 | Todd et al. |
| 5,489,262 A | 2/1996 | Cartmell et al. |
| 5,497,788 A | 3/1996 | Inman et al. |
| 5,520,629 A | 5/1996 | Heinecke et al. |
| 5,526,683 A | 6/1996 | Maggio |
| 5,527,274 A * | 6/1996 | Zakko ............................ 604/28 |
| 5,527,293 A | 6/1996 | Zamierowski |
| 5,538,502 A | 7/1996 | Johnstone |
| 5,549,584 A | 8/1996 | Gross |
| 5,556,375 A | 9/1996 | Ewall |
| 5,562,615 A | 10/1996 | Nassif |
| 5,607,388 A | 3/1997 | Ewall |
| 5,628,230 A | 5/1997 | Flam |
| 5,636,643 A | 6/1997 | Argenta et al. |
| 5,645,081 A | 7/1997 | Argenta et al. |
| 5,645,539 A | 7/1997 | Solomon et al. |
| 5,653,244 A | 8/1997 | Shaw |
| 5,690,815 A | 11/1997 | Krasnoff et al. |
| 5,808,181 A | 9/1998 | Wamsiedler et al. |
| 5,810,765 A | 9/1998 | Oda |
| 5,895,869 A | 4/1999 | Von Behrens et al. |
| 5,907,093 A | 5/1999 | Lehmann |
| 5,950,238 A | 9/1999 | Klein |
| 6,071,267 A | 6/2000 | Zamierowski |
| 6,086,450 A | 7/2000 | Mankovitz |
| 6,109,267 A | 8/2000 | Shaw et al. |
| 6,135,116 A | 10/2000 | Vogel et al. |
| 6,142,982 A | 11/2000 | Hunt et al. |
| 6,162,960 A | 12/2000 | Klein |
| 6,174,306 B1 | 1/2001 | Fleischmann |
| 6,241,747 B1 | 6/2001 | Ruff |
| 6,287,316 B1 | 9/2001 | Agarwal et al. |
| 6,302,653 B1 | 10/2001 | Bryant et al. |
| 6,345,623 B1 | 2/2002 | Heaton et al. |
| 6,361,397 B1 | 3/2002 | Mankovitz et al. |
| RE37,651 E | 4/2002 | Wallsten et al. |
| 6,402,714 B1 | 6/2002 | Kraft-Kivikoski |
| 6,420,622 B1 | 7/2002 | Johnston et al. |
| 6,440,093 B1 | 8/2002 | McEwen et al. |
| 6,488,643 B1 | 12/2002 | Tumey et al. |
| 6,493,568 B1 | 12/2002 | Bell et al. |
| 6,537,495 B1 | 3/2003 | Cambron et al. |
| 6,553,998 B2 | 4/2003 | Heaton et al. |
| 6,585,675 B1 | 7/2003 | O'Mahoney et al. |

| | | | |
|---|---|---|---|
| 6,626,891 B2 | 9/2003 | Ohmstede | |
| 6,648,862 B2 | 11/2003 | Watson | |
| 6,685,681 B2 | 2/2004 | Lockwood et al. | |
| 6,752,794 B2 | 6/2004 | Lockwood et al. | |
| 6,764,462 B2 | 7/2004 | Risk, Jr. et al. | |
| 6,767,188 B2 | 7/2004 | Vrane et al. | |
| 6,814,079 B2 | 11/2004 | Heaton et al. | |
| 6,824,533 B2 | 11/2004 | Risk et al. | |
| 6,855,135 B2 | 2/2005 | Lockwood et al. | |
| 6,867,342 B2 | 3/2005 | Johnston et al. | |
| D503,509 S | 4/2005 | Bell et al. | |
| 6,932,786 B2 | 8/2005 | Giacomelli et al. | |
| 6,979,324 B2 | 12/2005 | Bybordi et al. | |
| 7,070,584 B2 | 7/2006 | Johnston et al. | |
| 7,090,647 B2 | 8/2006 | Mimura et al. | |
| 7,135,007 B2 | 11/2006 | Scott et al. | |
| 7,144,294 B2 | 12/2006 | Bell et al. | |
| 7,195,624 B2 | 3/2007 | Lockwood et al. | |
| 7,201,263 B2 | 4/2007 | Osada et al. | |
| 7,252,014 B1 | 8/2007 | Mayer et al. | |
| 7,438,705 B2 | 10/2008 | Karpowicz et al. | |
| 7,670,323 B2 | 3/2010 | Hunt et al. | |
| 7,758,555 B2 | 7/2010 | Kelch et al. | |
| 7,927,319 B2 | 4/2011 | Lawhorn | |
| 2002/0065494 A1 | 5/2002 | Lockwood et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0032915 A1 | 2/2003 | Saul | |
| 2003/0040687 A1 | 2/2003 | Boynton et al. | |
| 2004/0064132 A1 | 4/2004 | Boehringer et al. | |
| 2004/0073151 A1 | 4/2004 | Weston | |
| 2005/0070858 A1 | 3/2005 | Lockwood et al. | |
| 2005/0137539 A1 | 6/2005 | Biggie et al. | |
| 2005/0148913 A1 | 7/2005 | Weston | |
| 2005/0197647 A1 | 9/2005 | Doliver et al. | |
| 2005/0261642 A1 | 11/2005 | Weston | |
| 2005/0261643 A1 | 11/2005 | Bybordi et al. | |
| 2006/0025727 A1 | 2/2006 | Boehringer et al. | |
| 2006/0122558 A1 | 6/2006 | Sherman et al. | |
| 2006/0173253 A1 | 8/2006 | Ganapathy et al. | |
| 2006/0189887 A1 | 8/2006 | Hassler, Jr. et al. | |
| 2006/0229531 A1 | 10/2006 | Goldberger et al. | |
| 2007/0032762 A1 | 2/2007 | Vogel | |
| 2007/0032763 A1 | 2/2007 | Vogel | |
| 2007/0055209 A1 | 3/2007 | Patel et al. | |
| 2007/0078444 A1 | 4/2007 | Larsson | |
| 2007/0118096 A1 | 5/2007 | Smith et al. | |
| 2007/0167927 A1 | 7/2007 | Hunt et al. | |
| 2007/0265586 A1 | 11/2007 | Joshi et al. | |
| 2008/0071235 A1 | 3/2008 | Locke et al. | |
| 2008/0125698 A1 | 5/2008 | Gerg et al. | |
| 2009/0099498 A1 | 4/2009 | Demers | |
| 2010/0022934 A1 | 1/2010 | Hogard | |

FOREIGN PATENT DOCUMENTS

| | | |
|---|---|---|
| AU | 745271 | 4/1999 |
| AU | 755496 | 2/2002 |
| CA | 2005436 | 6/1990 |
| CN | 2805782 Y | 8/2006 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 98/25122 A1 | 6/1998 |
| WO | WO 99/13793 | 3/1999 |
| WO | WO 00/21586 A1 | 4/2000 |
| WO | WO 03/101508 A | 12/2003 |
| WO | WO 2007/133618 A2 | 11/2007 |
| WO | WO 2008/036360 A | 3/2008 |
| WO | WO 2009/019496 A2 | 2/2009 |
| WO | WO 2009/071926 A1 | 6/2009 |

OTHER PUBLICATIONS

Final Office Action date mailed Oct. 29, 2010 for U.S. Appl. No. 12/070,891.

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Ð ukić, Ž. Maksimović, Ð . Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax, " *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

Lambert K.V. et al, "Vacuum assisted closure: a review of development and current applications", Eur. J. Vasc. Endovasc. Surg, 2005, vol. 29, No. 3, p. 219-26, Table 2.

NPD Negative Pressure Wound Therapy System, Kalypto Medical, pp. 1-4.

Laskin et al., "Minimally Invasive Total Knee Replacement Through a Mini-Midvastus Incision: An Outcome Study," Surgical Technology International XIII, 2004; 231-8.

Partial International Search Report date mailed Feb. 4, 2010; International Application No. PCT/US2009/053165.

Non-Final Office Action date mailed May 19, 2010 in U.S. Appl. No. 12/069,364.

Response filed Aug. 6, 2010 to Non-Final Office Action date mailed May 19, 2010 in U.S. Appl. No. 12/069,364.

Examiner Interview Summary date mailed Aug. 16, 2010 in U.S. Appl. No. 12/069,364.

Non-Final Office Action date mailed May 12, 2010 in U.S. Appl. No. 12/070,891.

Examiner Interview Summary date mailed Jul. 22, 2010 in U.S. Appl. No. 12/070,891.

Response filed Aug. 10, 2010 to Non Final Office Action date mailed May 12, 2010 in U.S. Appl. 12/070,891.

Restriction Requirement date mailed Sep. 22, 2009 in U.S. Appl. No. 11/901,664.

Response filed Oct. 22, 2009 to Restriction Requirement date mailed Sep. 22, 2009 in U.S. Appl. No. 11/901,664.

Non-Final Office Action date mailed Jan. 6, 2010 in U.S. Appl. No. 11/901,664.

Examiner Interview Summary date mailed Mar. 23, 2010 in U.S. Appl. No. 11/901,664.

Response filed Apr. 1, 2010 to Non-Final Office Action date mailed Jan. 6, 2010 in U.S. Appl. No. 11/901,664.

Final Office Action date mailed Jun. 4, 2010 in U.S. Appl. No. 11/901,664.

Examiner Interview Summary date mailed Jul. 26, 2010 in U.S. Appl. No. 11/901,664.

RCE/Response filed on Sep. 3, 2010 to Final Office Action date mailed Jun. 4, 2010 in U.S. Appl. No. 11/901,664.

Non-Final Office Action date mailed Apr. 2, 2008 in U.S. Appl. No. 11/903,165.

Response filed Jun. 26, 2008 to Non-Final Office Action date mailed Apr. 2, 2008 in U.S. Appl. No. 11/903,165.

Final Office Action date mailed Oct. 30, 2008 in U.S. Appl. No. 11/903,165.

RCE/Response filed on Jan. 30, 2009 in U.S. Appl. No. 11/903,165.

Non-Final Office Action date mailed Apr. 27, 2009 in U.S. Appl. No. 11/903,165.

Response filed Jul. 8, 2009 to Non-Final Office Action date mailed Apr. 27, 2009 in U.S. Appl. No. 11/903,165.

Final Office Action date mailed Sep. 30, 2009 in U.S. Appl. No. 11/903,165.

Examiner Interview Summary date mailed Dec. 11, 2009 in U.S. Appl. No. 11/903,165.

Response filed Jan. 27, 2010 to Final Office Action date mailed Sep. 30, 2009 in U.S. Appl. No. 11/903,165.

Request for Continued Examination filed Mar. 30, 2010 in U.S. Appl. No. 11/903,165.

Notice of Allowance date mailed Apr. 1, 2010 in U.S. Appl. No. 11/903,165.

Supplemental Notice of Allowance date mailed Apr. 21, 2010 in U.S. Appl. No. 11/903,165.

Supplemental Notice of Allowance date mailed May 14, 2010 in U.S. Appl. No. 11/903,165.

Supplemental Notice of Allowance date mailed Jun. 1, 2010 in U.S. Appl. No. 11/903,165.

Amendment after Final filed Dec. 20, 2010 for U.S. Appl. No. 12/069,364.

Advisory Action date mailed Jan. 3, 2011 for U.S. Appl. No. 12/069,364.

RCE/Response filed Feb. 24, 2011 for U.S. Appl. No. 12/069,364.

Response filed Dec. 15, 2010 for U.S. Appl. No. 12/070,891.

Notice of Allowance date mailed Dec. 23, 2010 for U.S. Appl. No. 12/070,891.

* cited by examiner

REDUCED PRESSURE TREATMENT SYSTEM HAVING BLOCKAGE CLEARING AND DUAL-ZONE PRESSURE PROTECTION CAPABILITIES

CROSS-REFERENCE TO RELATED APPLICATIONS

This application is a divisional of U.S. patent application Ser. No. 11/903,165 filed Sep. 19, 2007 now U.S. Pat. No. 7,758,555, which claims the benefit of U.S. Provisional Application No. 60/849,138, filed Oct. 2, 2006, and U.S. Provisional Application No. 60/845,993, filed Sep. 19, 2006. All of the above-mentioned applications are hereby incorporated by reference.

BACKGROUND OF THE INVENTION

1. Field of the Invention

The present invention relates generally to tissue treatment devices and in particular to a reduced pressure treatment system having blockage clearing and dual-zone pressure protection capabilities.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure has involved treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times.

While reduced pressure can greatly benefit wound care and other instances where increased tissue growth is indicated, the amount of reduced pressure applied to a tissue site must be controlled to prevent damage to tissue and the possibility of excessive bleeding. It is a common occurrence for blockages to develop in systems that provide reduced pressure therapy. The usual method for addressing these blockages involves the application of additional negative pressure. This additional negative pressure can present a hazard to the safe use of these devices. A need therefore exists for a reduced pressure treatment system and method that is capable of balancing the application of reduced pressure to encourage tissue growth, yet prevent over application of reduced pressure that may cause damage to the tissue.

BRIEF SUMMARY OF THE INVENTION

The problems presented in controlling the pressures applied by a tissue treatment system are solved by the systems and methods of the present invention. In one embodiment, a reduced pressure treatment system is provided that includes a reduced pressure source fluidly connected to a tissue site. A sensing device is provided in communication with the reduced pressure source to measure a source pressure at the reduced pressure source. A processing unit is in communication with the sensing device and is configured to determine a differential pressure between the source pressure and a desired tissue site pressure. The processing unit is further in communication with the reduced pressure source to regulate the source pressure applied by the reduced pressure source. The pressure is regulated such that the differential pressure does not exceed (a) a first maximum differential pressure if a blockage is present between the reduced pressure source and the tissue site and (b) a second maximum differential pressure if no blockage is present between the reduced pressure source and the tissue site.

In accordance with another embodiment of the present invention, a method of treating a tissue site is provided. The method includes applying a reduced pressure to a tissue site with a reduced pressure source. A source pressure is monitored at the reduced pressure source, and a differential pressure between the source pressure and the desired tissue site pressure is determined. If a blockage is present between the reduced pressure source and the tissue site, the differential pressure is limited to a first maximum differential pressure. If no blockage is present between the reduced pressure source and the tissue site, the differential pressure is limited to a second maximum differential pressure.

In still another embodiment of the present invention, a reduced pressure treatment system includes a means for applying reduced pressure to a tissue site and a means for monitoring a source pressure at the means for applying reduced pressure. The system further includes a means for determining a differential pressure between the source pressure and the desired tissue site pressure. A means is provided for limiting the differential pressure to a first maximum differential pressure if a blockage is present between the tissue site and the means for applying reduced pressure. The system further includes a means for limiting the differential pressure to a second maximum differential pressure that is higher than the first maximum differential pressure if no blockage is present between the tissue site and the means for applying reduced pressure.

Other objects, features, and advantages of the present invention will become apparent with reference to the drawings and detailed description that follow.

DETAILED DESCRIPTION OF THE PREFERRED EMBODIMENT

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Although the terms "vacuum" and "negative pressure" may be used to describe the pressure applied to the tissue site, the actual pressure applied to the tissue site may be significantly less than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure.

The term "tissue site" as used herein refers to a wound or defect located on or within any tissue, including but not limited to, bone tissue, adipose tissue, muscle tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Figure 1:
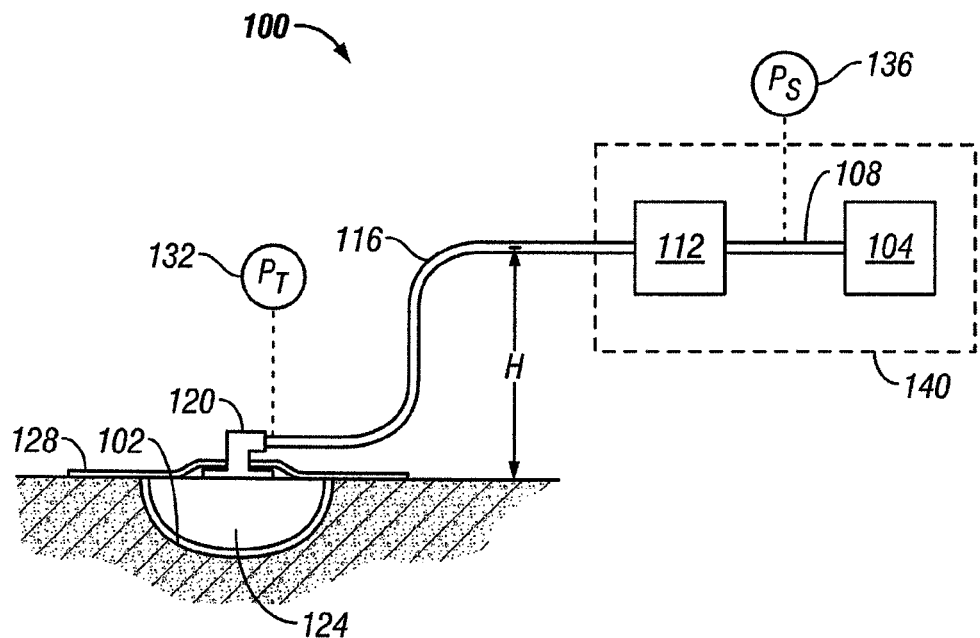
FIG. 1 illustrates a schematic of a reduced pressure treatment system having a reduced pressure therapy unit according to an embodiment of the present invention.

Referring to FIG. 1, a reduced pressure treatment system 100 according to an embodiment of the present invention is provided to deliver a reduced pressure to a tissue site 102 of a patient. The reduced pressure treatment system 100 includes a reduced pressure source 104 fluidly connected by a conduit 108 to a canister 112. The canister 112 is fluidly connected by a conduit 116 to a manifold adapter 120, which is in contact and fluid communication with a distribution manifold 124. Distribution manifold 124 is placed in contact with the tissue site 102. A drape 128 is positioned over the distribution manifold 124 and is preferably sealed to tissue surrounding the perimeter of the tissue site 102. The manifold adapter 120 preferably protrudes through the drape 128, and the drape 128 is sealed to the manifold adapter 120. The drape 128 may be made from an impermeable or semi-permeable material to assist in maintaining reduced pressure at the tissue site 102.

The distribution manifold 124 is primarily responsible for distributing reduced pressure to the tissue site 102, channeling exudates and other fluids away from the tissue site 102, inducing micro-deformation at the tissue site 102, and supporting the drape 128 to create a space in which reduced pressure is maintained. In practice, the distribution manifold 124 is typically an open-cell foam such as a reticulated polyurethane or polyvinyl alcohol foam. The open-cell foam is sized to fit the tissue site 102, placed into contact with the tissue 102, and then periodically replaced with smaller pieces of foam as tissue begins to grow and the tissue site 102 becomes smaller. Frequent replacement of the open-cell foam is necessary to minimize the in-growth of tissue into the cells of the foam. Despite the common use of open-cell foams, many alternative materials may be used as replaceable distribution manifolds, including gauze and any other materials capable of providing distribution characteristics. Similarly, non-replaceable, biocompatible materials may be used as a distribution manifold and then allowed to remain in place at the tissue site 102. In most cases, these biocompatible materials will serve as scaffolds for new tissue growth, and if bioresorbable, will be absorbed by the patient's body during or following treatment.

The reduced pressure treatment system 100 further includes a first sensing device 132 in communication with the tissue site 102 to measure a pressure at the tissue site 102. A second sensing device 136 is in communication with the reduced pressure source 104 to measure a source pressure at the reduced pressure source 104. The first and second sensing devices 132, 136 may be pressure sensors or any other type of sensors capable of determining a pressure of a fluid (i.e. a liquid or a gas). The first and second sensing devices 132, 136 may include processing units (not illustrated) to assist in collecting, interpreting, conditioning, or transmitting data. The physical connection between the sensing devices 132, 136 and the fluid components of the reduced pressure treatment system 100 may vary depending on the type of sensing device 132, 136 that is used. Similarly, the physical location at which each sensing device 132, 136 is connected to the fluid components of the reduced pressure treatment system 100 may vary as long as the desired pressure, or an approximation thereof, is being determined. The first sensing device 132 is illustrated in FIG. 1 as being physically connected to the conduit 116 near the manifold adapter 120. Although this is one possible configuration, in another embodiment, the first sensing device 132 is a pressure sensor and is fluidly connected through a measurement lumen of conduit 116 to the space beneath drape 128. By providing multiple lumens in conduit 116 (at least one for delivery of reduced pressure and at least one for measurement of the tissue site pressure), the first sensing device 132 may be located remotely from the tissue site 102. The first sensing device 132 may be placed in a variety of locations as long as the tissue site pressure determined by the first sensing device 132 substantially approximates the pressure to which the tissue site 102 is exposed.

With respect to the second sensing device 136, the second sensing device 136 may be connected to the conduit 108 (illustrated in FIG. 1) or to the canister 112 to determine the source pressure, which corresponds to the reduced pressure that is output by the reduced pressure source 104. Alternatively, the second sensing device 136 may be placed in communication with an output port of the reduced pressure source 104 to directly measure the amount of vacuum pressure being produced by the reduced pressure source 104.

Figure 2:
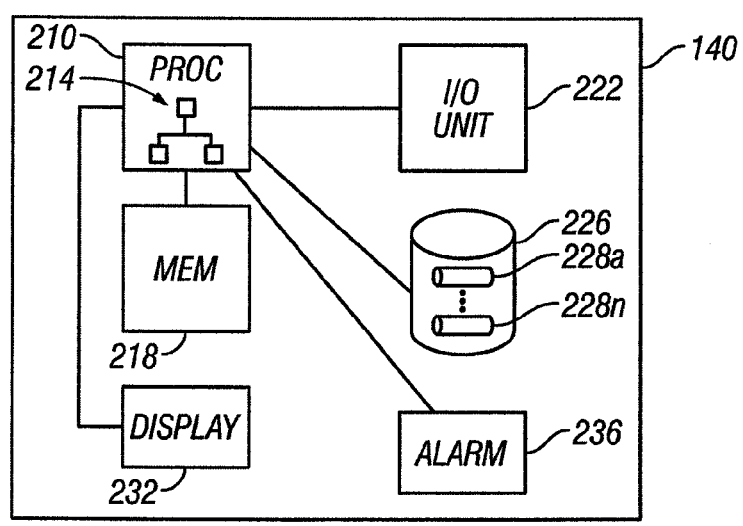
FIG. 2 depicts a block diagram of the reduced pressure therapy unit of FIG. 1.

Referring still to FIG. 1, but also to FIG. 2, the reduced pressure source 104 and the canister 112 may be contained within or mounted on a reduced pressure therapy unit 140. The therapy unit 140 may also contain first and second sensing devices 132, 136, as well as a processing unit 210 that executes software 214. The processing unit 210 may be configured with one or more processors that are the same or different types. For example, the processing unit 210 may include one or more processors, logic, analog components, or any other electronics that enable signals including information, such as fluid pressure at a tissue site, to be received.

The processing unit 210 may further be in communication with (i) a memory 218 for storing data and software code, (ii) an input/output (I/O) unit 222 for communicating with other devices and systems, such as a valves or sensing devices, wirelessly, via a wire, or via a memory input device (not shown), (iii) a storage unit 226 that may store one or more data repositories 228a-228n (collectively 228), such as a database having one or more files, (iv) an electronic display 232 that may or may not be touch-sensitive, and (v) an alarm 236 that is capable of signaling a user of the reduced pressure therapy unit 140 using audio, visual, or other signals. The software 214 may be configured to interface with each of the other devices (e.g., electronic display 232) to allow management and observation of the reduced pressure treatment.

The processing unit 210 is in communication with the first and second sensing devices 132, 136 to control the application of reduced pressure by the reduced pressure source 104. In operation, a target pressure is prescribed (preferably by a doctor or other approved medical personnel) for delivery to the tissue site 102. The target pressure is the "desired" reduced pressure to which the tissue site 102 should be exposed. The desired tissue site pressure will vary from tissue site to tissue site, but will generally be chosen based on the type of tissue making up the tissue site, the type of injury or wound (if any), the medical condition of the patient, and the preference of the attending physician. After selecting the desired tissue site pressure, the reduced pressure source 104 is operated to achieve the desired tissue site pressure at the wound. In many cases, the reduced pressure source 104 will need to be operated at a higher reduced pressure (i.e. lower absolute pressure) than that of the desired tissue site pressure due to pressure losses between the reduced pressure source 104 and the tissue site 102. Moreover, the head pressure of exudates and other fluids within the conduits may result in a reduction of vacuum pressure at the tissue site 102. In FIG. 1, the height, H, of the canister 112 above the tissue site 102 will determine the amount of head pressure imposed on the tissue site 102 by fluid in the conduit 116. For exudates and fluids with a density similar to water, the head pressure imposed by one foot of fluid is almost 25 mm Hg. Some fluids withdrawn from the tissue site may be heavier or more viscous than water, and therefore have a more pronounced effect on pressure losses at the tissue site 102.

As an example of the potential losses caused by the weight of fluid in the conduits, a prescribed target pressure for a particular tissue site may be −125 mm Hg. If the canister 112 is positioned four feet above the tissue site, and if the conduit 116 between the canister 112 and tissue site 102 is completely full of fluid, the head pressure imposed by that fluid could be almost 100 mm Hg. This particular example may be very common if a tissue site is located on a lower extremity of a patient such as a foot and the canister 112 is mounted near or above the patient's head (e.g., on an IV pole when the patient is in a wheelchair). If the head pressure of fluid in the conduit 116 is approximately 100 mm Hg, a source pressure of approximately −225 mm Hg would need to be applied to result in a tissue site pressure of −125 mm Hg.

Another factor that can reduce the tissue site pressure (relative to the source pressure) is a conduit blockage between the tissue site 102 and the reduced pressure source 104. A pressure differential between the pressure supplied by the reduced pressure source 104 (i.e. the source pressure) and the desired tissue site pressure 102 is important to monitor because of the possibility that the pressure differential is at least partially caused by a blockage. If a blockage exists, it is obviously important to clear the blockage as soon as possible. Blockages prevent application of prescribed target pressures, which result in treatment delays and slower healing. On the other hand, attempting to clear a blockage by applying additional pressure to the conduits can be dangerous if the differential pressure across the blockage becomes too great. When a blockage clears in the presence of a high reduced pressure (relative to the tissue site), this high reduced pressure is almost instantaneously communicated to the tissue site. The rapid onset of additional reduced pressure at the tissue site may cause damage to tissues and initiate excessive bleeding.

The reduced pressure treatment system 100 described herein provides protection against harm to the tissue site 102 caused by high negative pressures while providing the ability to overcome high head pressures under normal (no blockage) conditions. The system 100 employs a "dual-zone" approach, in which pressure differentials between the source pressure and the desired tissue site pressure are monitored and then compared to one of two maximum differential pressures depending on whether a blockage is present. More specifically, if a desired tissue site pressure for the tissue site 102 has not been met, the source pressure at the reduced pressure source 104 will be increased and monitored by second sensing device 136. As the source pressure continues to be increased, the differential pressure between the source pressure and the desired tissue site pressure is determined. The differential pressure may be calculated by the processing unit 210 after receiving data from the second sensing device 136. As long as the differential pressure does not exceed the first maximum differential pressure, the reduced pressure treatment system 100 attempts to achieve the desired tissue site pressure at the tissue site 102. The first sensing device 132 continues to monitor the tissue site 102 to determine if the pressure at the tissue site 102 reaches the desired tissue site pressure.

The reduced pressure source is not allowed to continue increasing the source pressure indefinitely. Instead, the source pressure is limited based on the differential pressure between the source pressure and the desired tissue site pressure. In an initial "safe" or "green-zone" operation, the differential pressure will not be allowed to exceed a first maximum differential pressure. It has been found that a sudden clearing of a blockage can result in the source pressure being applied directly to the wound site. It is therefore necessary to limit the absolute source pressure to a safe differential above the desired tissue site pressure. Clinical practice has shown that about 50 mm Hg is a safe amount of differential pressure, and in one embodiment, the first maximum differential pressure is set to about 50 mm Hg. More specifically, for most tissue sites, an instantaneous change of about 50 mm Hg reduced pressure will not cause harm to the tissue site. Under many "blockage" situations, a 50 mm Hg or less differential pressure is sufficient to clear the blockage. However, in the event that a blockage is not cleared by this amount of differential pressure, the reduced pressure treatment system 100 will not allow a further increase in reduced pressure simply to clear the blockage. Instead, the processing unit 210 communicates an alarm condition indicating a blockage to the alarm 236 and continues to apply reduced pressure within the green-zone parameters (i.e. differential pressure not to exceed about 50 mm Hg).

If the differential pressure reaches the first maximum differential pressure (i.e. about 50 mm Hg) and the target pressure still exceeds the tissue site pressure, then a blockage test is performed. When a change in source pressure at the reduced pressure source 104 does not result in a directionally corresponding change in the tissue site pressure, a blockage is present between the tissue site 102 and the reduced pressure source 104. If a directionally corresponding change does occur as the tissue site 102 as indicated by first sensing device 132, then a blockage is not present.

If the blockage test determines that a blockage is not present, and the tissue site pressure does not yet equal the desired tissue site pressure, the source pressure may be safely increased as there is no risk of sudden onset of additional pressure to the tissue site. In this "red-zone" operation, the differential pressure will not be allowed to exceed a second maximum differential pressure. In one embodiment, the second maximum differential pressure is about 100 mm Hg. Red-zone operating parameters are provided for situations when the reduced pressure treatment system 100 has confirmed the absence of blockages between the reduced pressure source 104 and the tissue site 102. This mode of operation may be particularly useful in situations where excessive fluid head pressures at the tissue site cause the tissue site pressure to be much lower than the desired tissue site pressure despite repeated increases in the source pressure.

While it is preferred that the first maximum differential pressure be 50 mm Hg and the second maximum differential pressure be 100 mm Hg, these pressure values could vary depending on the particular tissue site being treated and individual medical considerations. Although the pressure protection system described above is a "dual-zone" system, it should be apparent that a multi-zone system having more than two pressure parameters may be employed to provide additional protections.

Figure 3:
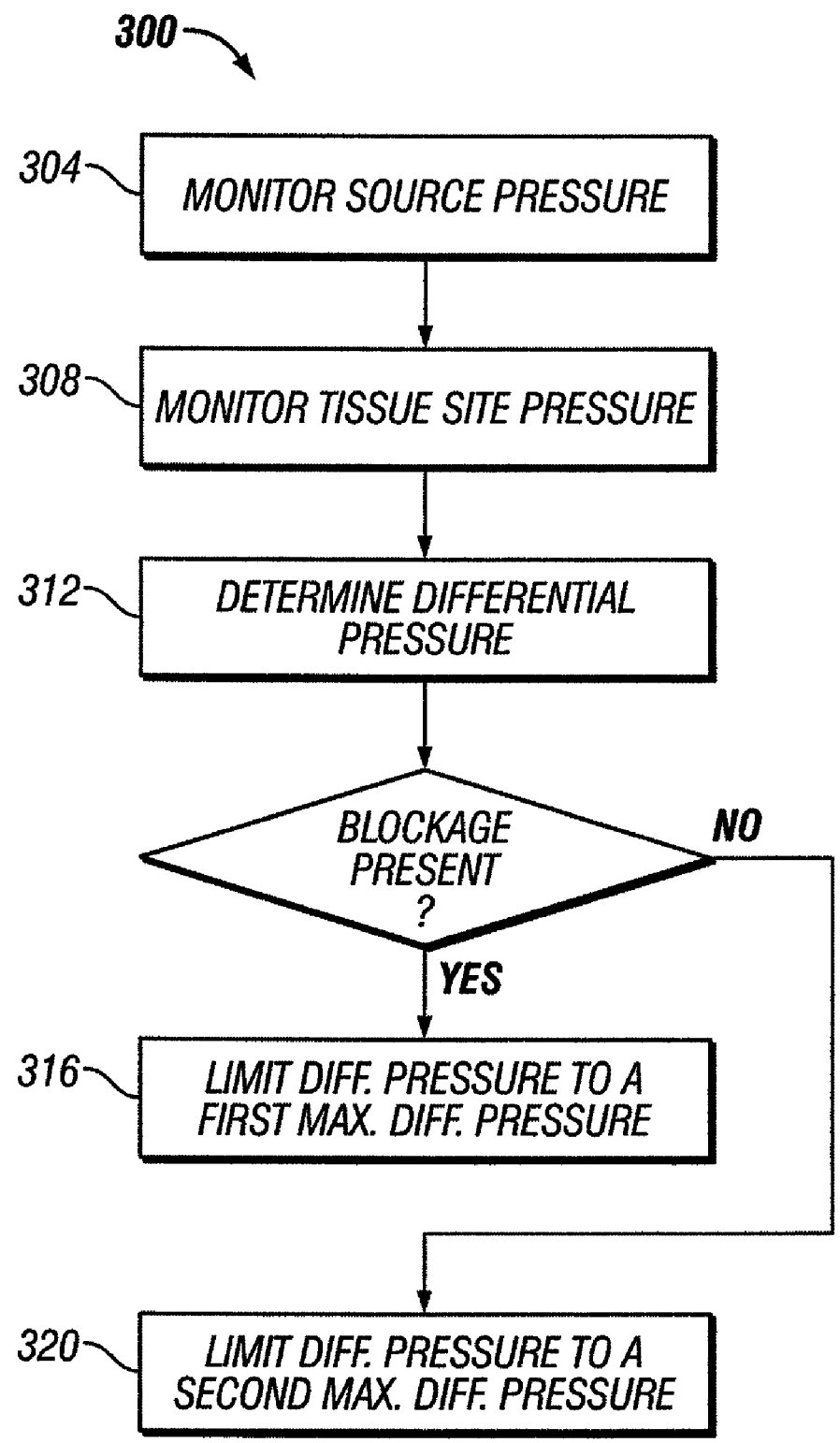
FIG. 3 illustrates a flow chart of an exemplary method of treating a tissue site according to an embodiment of the present invention.

Referring to FIG. 3, a method 300 of treating a tissue site according to an embodiment of the present invention includes monitoring a source pressure at a reduced pressure source 304, monitoring a tissue site pressure at a tissue site 308, and determining a differential pressure between the source pressure and the desired tissue site pressure. If a blockage is present between the reduced pressure source and the tissue site, the differential pressure is limited to a first maximum differential pressure at 316. If no blockage is present between the reduced pressure source and the tissue site, the differential pressure is limited to a second maximum differential pressure at 320.

It should be apparent from the foregoing that an invention having significant advantages has been provided. While the invention is shown in only a few of its forms, it is not just limited but is susceptible to various changes and modifications without departing from the spirit thereof.

We claim:

1. A method of treating a tissue site comprising:
   applying a reduced pressure to a tissue site with a reduced pressure source;
   monitoring a source pressure at the reduced pressure source;
   determining a differential pressure between the source pressure and the desired tissue site pressure;
   if a blockage is present between the reduced pressure source and the tissue site, limiting the differential pressure to a first maximum differential pressure; and
   if no blockage is present between the reduced pressure source and the tissue site, limiting the differential pressure to a second maximum differential pressure, wherein the second maximum differential pressure is greater than the first maximum differential pressure.

2. The method according to claim 1, wherein the first maximum differential pressure is about 50 mm Hg.

3. The method according to claim 1, wherein the second maximum differential pressure is about 100 mm Hg.

4. The method according to claim 1, wherein the step of determining the differential pressure further comprises monitoring the differential pressure.

5. The method according to claim 1 further comprising:
   when a blockage is present, increasing the source pressure, within the limits of the first maximum differential pressure, to attempt to clear the blockage.

6. The method according to claim 1 further comprising:
   when a blockage is present, increasing the source pressure, within the limits of the first maximum differential pressure, to attempt to clear the blockage; and
   if the blockage does not clear, generating an alarm to indicate that a blockage is present.

7. The method according to claim 1 further comprising:
   changing the source pressure, within the limits of one of the first and second maximum differential pressures, to cause a pressure at the tissue site to reach a desired tissue site pressure.

8. The method according to claim 1 further comprising:
   determining if a blockage is present by changing the source pressure and monitoring for a directionally corresponding change in a pressure at the tissue site; and
   determining that a blockage is present when no directionally corresponding change occurs in the pressure at the tissue site.

9. The method according to claim 8, wherein changing the source pressure further comprises increasing the source pressure.

* * * * *